United States Patent [19]

Lawrence

[11] 4,066,697

[45] Jan. 3, 1978

[54] PROCESS FOR PREPARING TETRAMETHYLTHIURAM TETRASULFIDE

[75] Inventor: John P. Lawrence, Stow, Ohio

[73] Assignee: The Goodyear Tire & Rubber Company, Akron, Ohio

[21] Appl. No.: 700,233

[22] Filed: June 28, 1976

[51] Int. Cl.² .......................................... C07C 155/10
[52] U.S. Cl. ................................................... 260/567
[58] Field of Search ........................................ 260/567

[56] References Cited

U.S. PATENT DOCUMENTS

| | | | |
|---|---|---|---|
| 1,681,717 | 8/1928 | Whitby | 260/567 |
| 1,782,111 | 11/1930 | Adams et al. | 260/567 |

OTHER PUBLICATIONS

Mallinckrodt, "Ar's Laboratory Chemicals", 4352 (1960).

*Primary Examiner*—Nicky Chan
*Attorney, Agent, or Firm*—F. W. Brunner; J. A. Rozmajzl

[57] ABSTRACT

Tetramethylthiuram tetrasulfide can be prepared in high yields by oxidation of an aqueous solution of dimethylammonium dimethyldithiocarbamate in the presence of carbon disulfide and sulfur. The process is essentially pollution free.

2 Claims, No Drawings

PROCESS FOR PREPARING TETRAMETHYLTHIURAM TETRASULFIDE

This invention relates to a process of preparing tetramethylthiuram tetrasulfide (TMTT).

A great deal of discrepancy exists in the literature regarding the chemical constitution of the materials commonly referred to as tetramethylthiuram tetrasulfide (TMTT). Whitby (U.S. Pat. No. 1,780,545) reported the preparation of TMTT by reaction of metal dithiocarbamates with sulfur monochloride in a mixture of ether and petroleum ether. Levi (Gazz Chim Ital. 61 373 [1931]) subsequently found that Whitby's reaction product was a mixture of the disulfide and hexasulfide. Levi reported that if the ammonium salt was used in the place of the metal salt the product of the reaction with sulfur monochloride was a mixture of the disulfide and sulfur. Issoire & Musso (Mem Poudres, 42 427 [19601]) reacted sulfur monochloride with aqueous sodium dimethyldithiocarbamate to form what they refer to as TMTT. This procedure has been repeated and the product found to contain approximately 10 percent more sulfur than would be contained in the tetrasulfide alone. Analysis also indicates the pressure of at least three components. The lack of analytical techniques to distinguish between mixtures of polysulfides and mixtures of polysulfides and sulfur has added confusion to the issue.

Adams (U.S. Pat. No. 1,782,111) described a process for manufacturing tetramethylthiuram disulfide involving the oxidation of dimethylammonium dimethyldithiocarbamate with hydrogen peroxide in the presence of carbon disulfide. He does not teach how to prepare the tetrasulfide.

It is an object of the present invention to provide the process for preparing TMTT in a nonpolluting manner avoiding the use of such reactants as sulfur monochloride which is a corrosive and malodorous compound. It is another object of the present invention to provide a method of preparing TMTT in high yield. Other objects of the present invention will become apparent as the description proceeds.

The objects of the present invention are accomplished by the oxidation of dimethylammonium dimethyldithiocarbamate (DADDC) in an aqueous medium with hydrogen peroxide in the presence of carbon disulfide and sulfur to provide a high yield of TMTT.

The reactants can be added in any order to the aqueous medium with the proviso that no reactants can be added subsequent to the hydrogen peroxide. The molar ratio of the DADDC to the carbon disulfide to the hydrogen peroxide is generally about 1/1/1. Normally about two gram atoms of sulfur is charged per one mol of DADDC. The molar ratio is important only with regard to the efficiency of the reaction.

One embodiment of the present invention involves reacting, in a first step, dimethylamine (DMA), preferably about two mols, with one mol of carbon disulfide in water to form DADDC. Excess carbon disulfide can be used if desired to provide carbon disulfide for the second step described below. The hydrogen peroxide and sulfur can then be added to the aqueous solution of the DADDC, as the second step, without isolating the DADDC therefrom, again with the proviso that no reactant is added subsequent to the hydrogen peroxide. If sufficient unreacted carbon disulfide, i.e., about one mol per mol of DADDC, is left available after the first reaction is completed, no additional carbon disulfide need be added for the oxidation reaction. Otherwise, additional carbon disulfide should be added to the DADDC solution to bring the total unreacted carbon disulfide level to about one mol per mol of DADDC. Preferably the carbon disulfide is used in slight excess (about 0.05 to 0.10 mol excess).

The concentration of the DADDC in the water generally ranges from 5 to 50 weight percent, but preferably in the range of 9 to 20 percent.

The hydrogen peroxide is naturally added to the aqueous reaction medium in aqueous form.

The sulfur is generally just added as a solid.

Although the process may be carried out under any pressure conditions no beneficial effect is derived from carrying out the process at pressures other than atmospheric pressure.

The exact nature of the product herein referred to as TMTT has not yet been determined due to lack of analytical procedures. The product has a higher melting point (131° C.) than products obtained by prior methods, strongly indicating that it has a somewhat different composition. In addition, analysis by thin layer chromatography suggests the presence of only one compound. Elemental analysis agrees very closely with the calculated values for TMTT. Although the results are not conclusive it could be that the present process produces pure or nearly pure TMTT. Nonetheless, whatever its composition, the compound is a sulfur donor for the sulfur vulcanization of rubber.

This process avoids the wasteful production of an undesirable by-product, sodium chloride, which is formed in the prior art method of reacting sodium dimethyldithiocarbamate with sulfur monochloride. The only by-product of the present process is water.

The product is formed as a solid suspended in the aqueous medium and can be isolated by any convenient means such as filtration or centrifugation.

The normal, but not limiting, molar ratios of reactants based on one mol of DADDC are as follows:

|  | Broad | Preferred |
|---|---|---|
| Carbon disulfide | 1–1.2 | 1–1.1 |
| Hydrogen peroxide | 1–1.2 | 1–1.1 |
| Sulfur | 2–2.2 | About 2 |

No catalyst for the reaction is required.

The oxidation reaction of the present invention is an exothermic one. The hydrogen peroxide is normally added at room temperature, for example, in the 20° C. to 30° C. range. Since the reaction is exothermic the temperature, unless controlled, rises during the reaction. The temperature rise will vary in degree depending upon such variables as the reactor used, but is typically 20° to 30° C. A total reaction temperature range is typically from 10° to 80° C., a preferred range being 20° to 65° C. In selecting a reaction temperature or reaction temperature range one should consider such factors as reactant solubility. For example, if the reaction were run at a controlled temperature of 10° C., although the desired product would be formed the yield would be lower than that obtained at a higher temperature.

The above remarks concerning temperature should be construed solely as guidelines and not as limitations.

The following examples are representative of the procedures used to prepare tetramethylthiuram tetrasulfide by the process of this invention.

EXAMPLE 1

The reactor consisted of a 2 liter resin kettle equipped with a stainless steel baffle and fitted with a turbine agitator, reflux condenser and thermometer. The reactor was charged with 300 milliliters of water, 111 grams (1.0 mol) of 40.4 percent aqueous dimethylamine and 2 drops of a nonionic surfactant. The solution at 25° C. was agitated at 570 RPM and 30 milliliters (0.5 mol) of carbon disulfide added over 14 minutes. The temperature increased to 35° C. Sulfur (32 grams, 1.0 gram atoms) was added in one portion followed by 300 milliliters of water. The temperature fell to 27° C. Next, 33 milliliters (0.55 mol) of carbon disulfide was added to the resulting slurry over 60 minutes concurrently with 164 milliliters (0.525 mol) of 3.2 molar hydrogen peroxide. The peroxide addition was started 2 minutes after the carbon disulfide addition was begin to ensure a slight excess (0.05 mol) of carbon disulfide was present. Both additions finished at the same time. The final temperature was 51° C. The light yellow solid product was filtered, washed with water and dried at 60° C. The yield was 138.2 grams (90% based on dimethylamine) with a melting point of 131° C. An elemental analysis of the product showed the following percentages: C — 23.37; H — 4.05; N — 9.09; S — 63.24. The calculated percentages for TMTT are: C — 23.68; H — 3.95; N — 9.21; and S — 63.16.

EXAMPLE 2

The procedure was the same as described in Example 1 except that the total charge of carbon disulfide (63 milliliters) was added to the dimethylamine solution, followed by the sulfur, additional water (300 milliliters) and finally the addition of hydrogen peroxide over 58 minutes. The yield was 137.4 grams. (90.4% based on dimethylamine) with a melting point of 125° - 128° C.

EXAMPLE 3

The procedure was the same as described in Example 1 except that the baffle was removed from the reactor and an 11 centimeter Teflon paddle agitator was used in place of the turbine agitator. The yield was 135.4 grams (89.1% based on dimethylamino) with a melting point of 129° - 131° C.

TMTT prepared by this process was found to be equivalent to TMTT prepared by prior art methods as a sulfur donor.

While certain representative embodiments and details have been shown for the purpose of illustrating the invention it will be apparent to those skilled in this art various changes and modifications may be made therein without departing from the spirit or scope of the invention.

What is claimed is:

1. A process of preparing a sulfur donor for the sulfur vulcanization of rubber comprising oxidizing dimethylammonium dimethyl dithiocarbamate with hydrogen peroxide in the presence of carbon disulfide and sulfur in water with the proviso that no reactant is added subsequent to the addition of the hydrogen peroxide wherein the molar ratio of dimethylammonium dimethyl dithiocarbamate to carbon disulfide to hydrogen peroxide to sulfur is about 1:1–1.2:1–1.2:2–2.2.

2. The process of claim 1 wherein the dimethylammonium dimethyldithiocarbamate is in the form of an aqueous solution prepared by reacting a combination comprising dimethylamine and carbon disulfide in water.

* * * * *